US007122347B2

(12) United States Patent
Verheije et al.

(10) Patent No.: US 7,122,347 B2
(45) Date of Patent: Oct. 17, 2006

(54) CHIMERIC ARTERIVIRUS-LIKE PARTICLES

(75) Inventors: Monique Helene Verheije, Dronten (NL); Johanna Jacoba M. Meulenberg, Amsterdam (NL)

(73) Assignee: Boehringer Ingelheim Vetmedica Gmbh, Ingelheim (DE)

( * ) Notice: Subject to any disclaimer, the term of this patent is extended or adjusted under 35 U.S.C. 154(b) by 192 days.

(21) Appl. No.: 10/300,699

(22) Filed: Nov. 19, 2002

(65) Prior Publication Data

US 2003/0161845 A1 Aug. 28, 2003

Related U.S. Application Data

(63) Continuation of application No. PCT/NL01/00382, filed on May 21, 2001.

(51) Int. Cl.
*C12P 21/06* (2006.01)

(52) U.S. Cl. .......................................... 435/69.1; 435/6

(58) Field of Classification Search ............. 424/204.1; 435/235.1, 69.1, 6; 530/30
See application file for complete search history.

(56) References Cited

U.S. PATENT DOCUMENTS 6,268,199 B1 7/2001 Meulenberg et al.

FOREIGN PATENT DOCUMENTS

| | | | |
|---|---|---|---|
| EP | 0 835 929 A1 | | 7/1997 |
| EP | 0 839 912 A1 | | 5/1998 |
| WO | WO 98/18933 | * | 5/1998 |
| WO | WO 98/55626 | | 12/1998 |
| WO | WO 00/53787 | | 9/2000 |

OTHER PUBLICATIONS

PCT International Search Report, PCT/NL01/00382, dated Sep. 12, 2001.

De Vries et al., Genetic Manipulation of Equine Arteritis Virus Using Full-Length cDNA Clones: Separation of Overlapping Genes and Expression of a Foreign Epitope, Virology, 2000, pp. 84-97, vol. 270.

* cited by examiner

*Primary Examiner*—Ali R. Salimi
(74) *Attorney, Agent, or Firm*—Thomas C. Blankinship; Michael P. Morris; Timothy X. Witkowski

(57) ABSTRACT

The invention relates to the field for Arteriviruses and vaccines directed against infections caused by these viruses. The invention provides an Arteriviruses-like particle comprising at least a first structural protein derived from a first Arterivirus and a second structural protein wherein the second structural protein is at least partly not derived from said first Arterivirus.

3 Claims, 3 Drawing Sheets

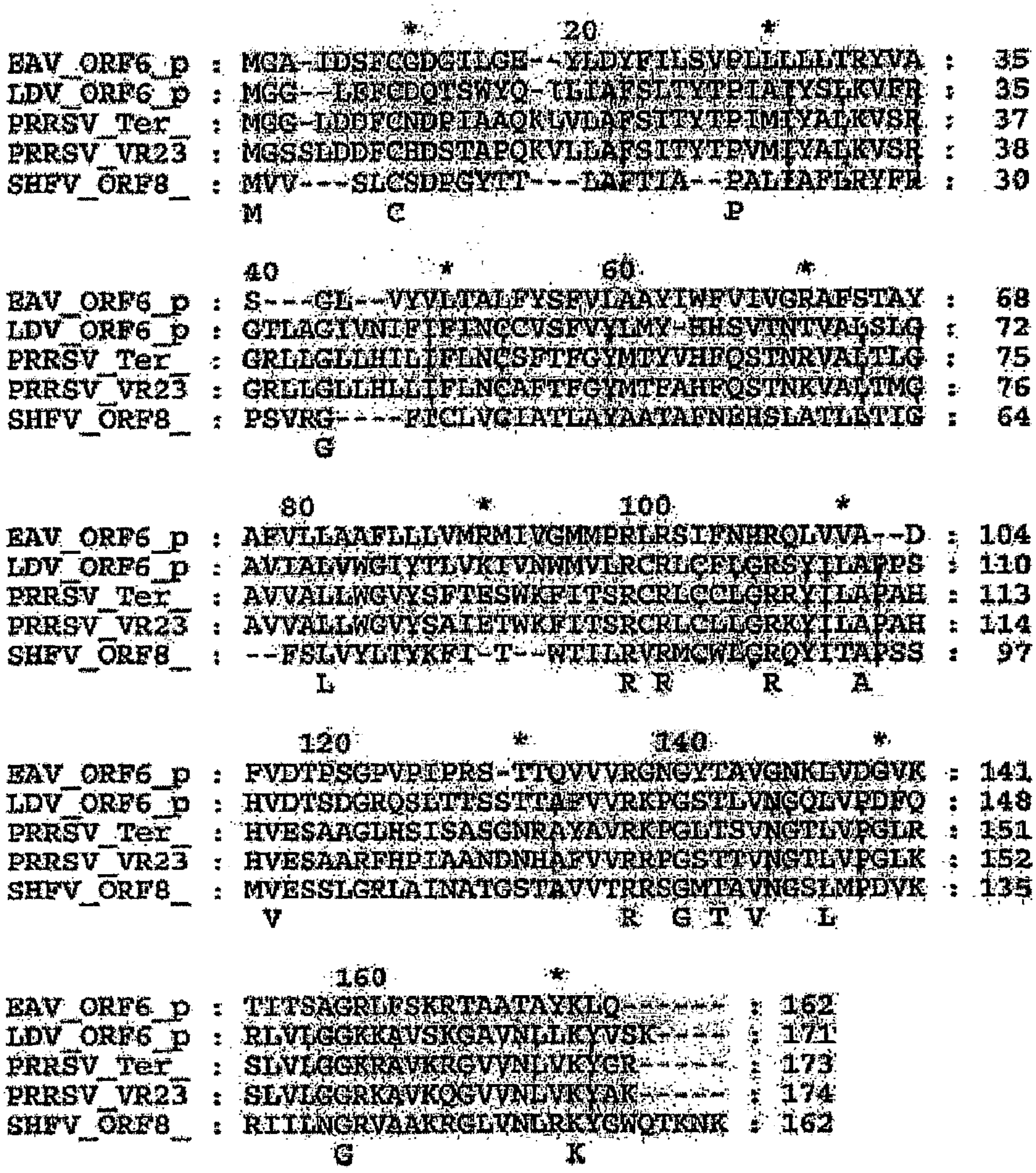

FIGURE 1

Figure 3:
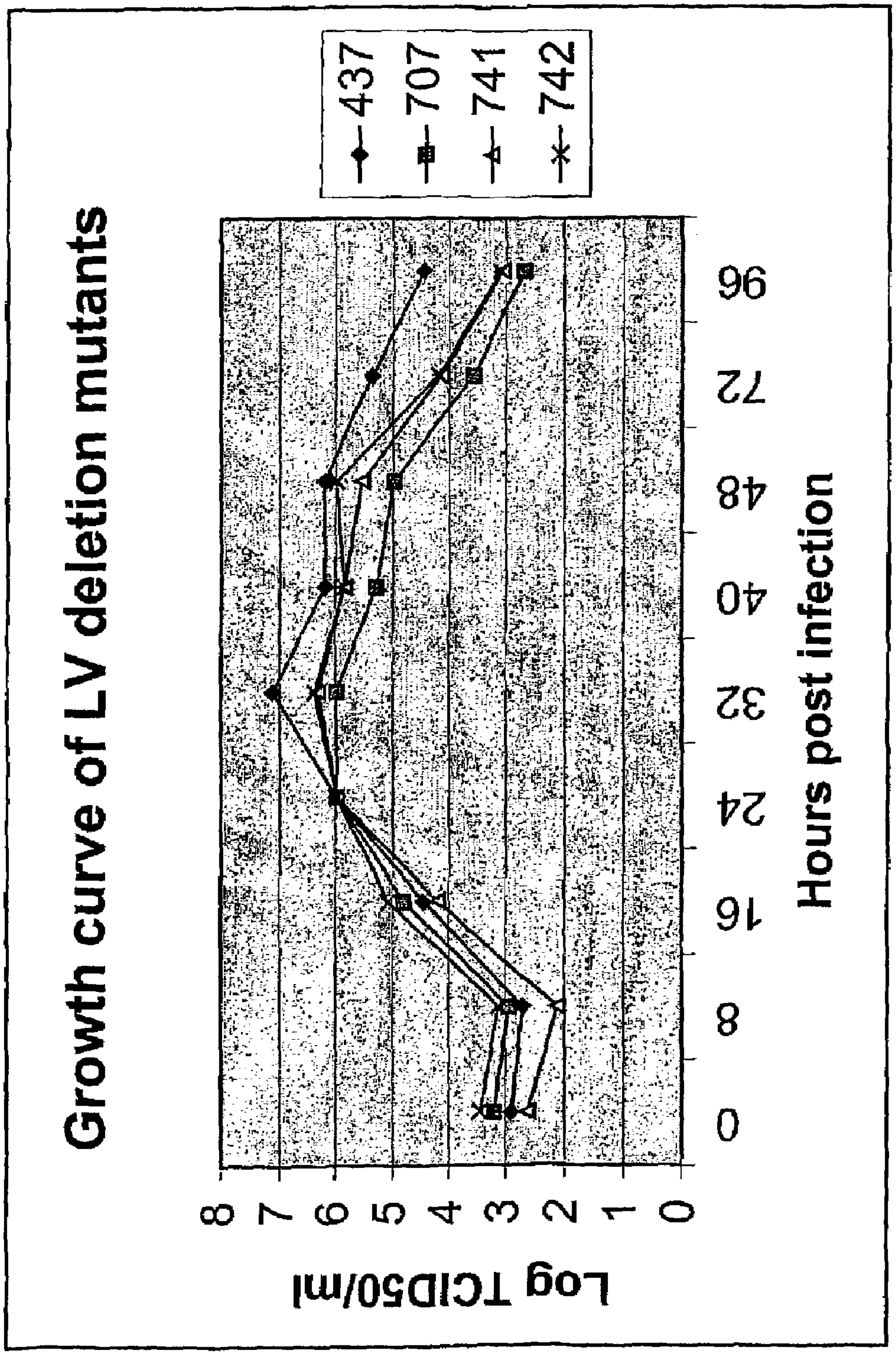

```
                         *           20                *
EAV_ORF6_p  : MGA-IDSFCGDGILGE--YLDYFILSVPLLLLLTRYVA  :  35
LDV_ORF6_p  : MGG--LEFCDQTSWYQ-TLIAFSLTYTPIATYSLKVFR  :  35
PRRSV_Ter_  : MGG-LDDFCNDPIAAQKLVLAFSTTYTPIMIYALKVSR  :  37
PRRSV_VR23  : MGSSLDDFCHDSTAPQKVLLAFSITYTPVMIYALKVSR  :  38
SHFV_ORF8_  : MVV---SLCSDEGYTT---LAFTIA--PALIAFLRYFR  :  30
                M   C                          P

                40          *           60             *
EAV_ORF6_p  : S---GL--VYVLTALFYSFVLAAYIWFVIVGRAFSTAY  :  68
LDV_ORF6_p  : GTLAGIVNIFTFINCCVSFVYLMY-HHSVTNTVALSLG  :  72
PRRSV_Ter_  : GRLLGLLHILIFLNCSFTFGYMTYVHFQSTNRVALTLG  :  75
PRRSV_VR23  : GRLLGLLHLLIFLNCAFTFGYMTFAHFQSTNKVALTMG  :  76
SHFV_ORF8_  : PSVRG----FICLVGIATLAYAATAFNEHSLATLLTIG  :  64
                G

                    80          *          100            *
EAV_ORF6_p  : AFVLLAAFLLLVMRMIVGMMPRLRSIFNHRQLVVA--D  :  104
LDV_ORF6_p  : AVIALVWGIYTLVKIVNWMVLRCRLCFLGRSYILAPPS  :  110
PRRSV_Ter_  : AVVALLWGVYSFTESWKFITSRCRLCCLGRRYILAPAH  :  113
PRRSV_VR23  : AVVALLWGVYSAIETWKFITSRCRLCLLGRKYILAPAH  :  114
SHFV_ORF8_  : --FSLVYLTYKFI-T--WTILRVRMCWLGRQYITAPSS  :  97
                L                 R R    R       A

                   120          *          140           *
EAV_ORF6_p  : FVDTPSGPVPIPRS-TTQVVVRGNGYTAVGNKLVDGVK  :  141
LDV_ORF6_p  : HVDTSDGRQSLTTSSTTAFVVRKPGSTLVNGQLVPDFQ  :  148
PRRSV_Ter_  : HVESAAGLHSISASGNRAYAVRKPGLTSVNGPLVPGLR  :  151
PRRSV_VR23  : HVESAARFHPIAANDNHAFVVRKPGSTTVNGTLVPGLK  :  152
SHFV_ORF8_  : MVESSLGRLAINATGSTAVVTRRSGMPAVNGSLMPDVK  :  135
                V                  R  G T  V    L

                   160         *
EAV_ORF6_p  : TITSAGRLFSKRTAATAYKLQ-----  :  162
LDV_ORF6_p  : RLVLGGKKAVSKGAVNLLKYVSK---  :  171
PRRSV_Ter_  : SLVLGGKRAVKRGVVNLVKYGR----  :  173
PRRSV_VR23  : SLVLGGRKAVKQGVVNLVKYAK----  :  174
SHFV_ORF8_  : RIILNGRVAAKRGLVNLRKYGWQTKNK  :  162
                G                K
```

FIGURE 2

A

```
pABV437 GP5   A  E  Q  W  E  A     *
          ...GCTGAGCAATGGGAGGC---CTAGACGATTTTTGCAACGATCCTATCGCCGCACAAAAG...
                      M  G  G  -  L  D  D  F  C  N  D  P  I  A  A  Q  K     M protein

pABV857 GP5   A  E  Q  W  G  R  P  *
          ...GCTGAGCAATGGGGTCGTCCTTAGATGACTTCTGTCATGATAGCACGGCTCCACAAAAG...
                      M  G  S  S  L  D  D  F  C  H  D  S  T  A  P  Q  K     M protein

pABV707 GP5   A  E  Q  W  E  A     *
          ...GCTGAGCAATGGGAGGC---CTA---GAATTTTGTGATCAAACTTCCTGGTATCAG---...
                      M  G  G  -  L  -  E  F  C  D  Q  T  S  W  Y  Q  -     M protein

pABV856 GP5   A  E  Q  W  E  P     *
          ...GCTGAGCAATGGGAGCC---ATAGATTCATTTTGTGGTGACGGGATTTTAGGTGAG---...
                      M  G  A  -  I  D  S  F  C  G  D  G  I  L  G  E  -     M protein
```

B

```
pABV871 GP5   A  E  Q  W  E  A  *
          ...GCTGAGCAGTGGGAAGCTTGATGGGAGGC---CTAGACGATTTTTGCAACGATCCTATCGCCGCACAAAAG...
                              M  G  G  -  L  D  D  F  C  N  D  P  I  A  A  Q  K  M protein

pABV872 GP5   A  E  Q  W  E  A  *
          ...GCTGAGCAGTGGGAAGCTTGATGGGGTCGTCCTTAGATGACTTCTGTCATGATAGCACGGCTCCACAAAAG...
                              M  G  S  S  L  D  D  F  C  H  D  S  T  A  P  Q  K  M protein

pABV873 GP5   A  E  Q  W  E  A  *
          ...GCTGAGCAGTGGGAAGCTTGATGGGAGCC---ATAGATTCATTTTGTGGTGACGGGATTTTAGGTGAG---...
                              M  G  A  -  I  D  S  F  C  G  D  G  I  L  G  E  -  M protein
```

CHIMERIC ARTERIVIRUS-LIKE PARTICLES

CROSS-REFERENCE TO RELATED APPLICATION

This application is a continuation of PCT International Patent Appln. No. PCT/NL01/00382, filed on May 21, 2001, designating the United States of America, and published, in English, as International Publication No. WO 01/90363 A1 (Nov. 29, 2001), the contents of the entirety of which is incorporated by this reference.

TECHNICAL FIELD

The invention generally relates to veterinary medicine, and particularly to Arteriviruses and vaccines directed against infections caused by these viruses.

BACKGROUND

Porcine reproductive and respiratory syndrome virus (PRRSV) is a positive-strand RNA virus that belongs to the family of arteriviruses together with equine arteritis virus (EAV), lactate dehydrogenase-elevating virus (LDV) and simian hemorrhagic fever virus (SHFV, 14). PRRSV causes reproductive failure in pregnant sows and respiratory problems in piglets (20). It causes huge economic losses in -pig populations world wide. EAV causes reproductive failure and abortions in mares, and leads to persistently infected stallions. Infections with LDV or SHFV are mainly of importance as infections of experimental animals in the laboratory.

Vaccination against these Arterivirus infections is often cumbersome. Killed vaccines, in general, are not effective enough for most purposes, and although live-attenuated Arterivirus vaccines are available, it has been shown that some of these are not safe and still spread. Furthermore, these vaccines can not be distinguished from wild type field virus.

The genome of PRRSV, as an example of an Arterivirus genome, is 15.1 kb in length and contains genes encoding the RNA dependent RNA polymerase (ORFIa and ORFIb) and genes encoding structural proteins (ORFs 2 to 7; (14), (11)). Other Arterivirus genomes are somewhat smaller, but share the same genomic build-up, in that all synthesize subgenomic messenger RNA encoding the structural proteins.

The ORFs 2, 3, and 4 encode glycoproteins designated GP2, GP3, and GP4, respectively. ORF5 encodes the major envelope glycoprotein, designated GP5, ORF6 encodes the membrane protein M, and ORF7 encodes the nueleocapsid protein N. An additional structural protein (GP2b) is encoded by a small OFR, ORF2b. The analysis of the genome sequence of PRRSV isolates from Europe and North America, and their reactivity with monoclonal antibodies has indicated that; isolates from these continents are genetically distinct and must have diverged from a common ancestor relatively long ago (15).

DISCLOSURE OF THE INVENTION

The invention provides an Arterivirus-like particle comprising at least a first structural protein derived from a first Arterivirus and a second structural protein wherein said second structural protein is at least partly not derived from said first Arterivirus. In a preferred embodiment, the invention provides a chimeric Arterivirus that is composed of parts originating from at least two different arteriviruses. Said parts are encoded by genes (or parts thereof) originating from said different arteriviruses, and that are preferably at least partly exchanged or substituted for each other. (Note that substitution does nor comprise a mere addition of a second structural protein (such as is disclosed in de Vries et al Virol. 270:84–97) where a stretch of nucleic acids encoding a non-Arteriviris protein fragment is inserted in the full genome of an Arterivirus, thereby extending said genome without an exchange of parts as provided herein. In a preferred embodiment of the invention said chimeric arterivirus as provided exhibits distinct characteristics of the composing arteriviruses.

Said second part that is not derived from the first Arterivirus can for example comprise a fully but preferably only partially artificial or synthetic sequence, encoding in frame a stretch of amino acids of distinct length allowing for functional dimerisation with said first structural protein as shown herein, thereby allowing heterodimerisation. A heterodimer is a composition of two different interacting peptide chains. The interaction may for example consist of both Van derWaals forces or covalent disulfide bonds, but are not limited to this. It was found that said heterodimerisation, preferably of two glycoproteins, or of a glycoprotein and the matrix or membrane protein, enhances the structural integrity of the resulting chimeric virus particle, thereby allowing a better presentation of immunologically important domains on the particle and making it a better vaccine constituent.

Besides that said part being involved in heterodimerisation should be a structural protein (non-structural proteins are no part of the particle) it is thus preferred that said part that is not derived from a first Arterivirus at least has a certain measure of homology with said second Arterivirus, e.g. to allow for functional dimerisation. A further condition relevant for heterodimerisation is that in general the nucleoprotein (N) should not be involved, the nucleoprotein of particles as provided in EP 0 839 912 does not contribute to the phenomenon. However, such a particle as provided herein can for example be based on an infectious cDNA clone of an Arterivirus (13; EP 0 839 912), as also described in WO 98/55626 where a recombinant virus is described comprising a combination of non-structural proteins (from genes encoding open reading frames 1*a* and 1*b*, such as the viral poymerase) of a first Arterivirus with the structural proteins (from genes encoding open reading frames 2 to 7) of a second. An infectious clone is an excellent tool for site-directed mutagenesis and is important for projects whose aim is to construct new live vaccines against Arteriviruses. Herein we for example provide a so-called marker vaccine by mutagenesis of the genome, so that, in the case of for example PRRSV, vaccinated pigs (i.e. vaccinated with a vaccine as provided herein) can be distinguished or discriminated from field virus-infected pigs on the basis of differences in serum antibodies, and vice-versa, on the basis of differences in serum antibodies. Such discrimination can in particular well be done when said second structural protein is at least partly not derived from said first Arterivirus, and antibodies directed against said artificial, synthetic or heterologous part can thus be detected, or, alternatively, vaccinated animals are detectable in diagnostic tests by the absence of antibodies directed against the homologous, now absent, structural protein or part thereof. It is preferred that said second structural protein is the nucleocapsid (N) protein since antibodies directed against N are often overabundant, especially in natural infections, and allow for discrimination of vaccinated from non-vaccinated but infected animals. In particular the invention provides a particle wherein said second structural protein is at last partly derived from a second Arterivirus, or at least has a certain measure (e.g. >50%) of homology with said second Arterivirus. A particle as provided herein is also called an inter-Arterivirus or -virus-like chimeric particle, and can of course also comprise stretches on nucleic acid that are not Arterivirus derived, for example encoding non-Arterivirus pathogens or antigens thereof. Particularly useful is such a particle wherein said first and second structural protein comprise a heterodimer, e.g. linked by a disulfide bridge between two cysteines. Most preferred is a particle according to the invention wherein said first or second structural protein comprises a integral membrane protein (M) or part thereof.

The M protein (18 kDa) is non-glycosylated and is the most conserved structural protein of arteriviruses. For PRRSV, its topology and membrane-associated function is first suggested by Meulenberg et al (14). The N-terminal half of the protein is suggested to have three potential membrane-spanning regions, the N-terminus comprises an ectodomain part, the C-terminus comprises an endodomain part. A stretch of 16 amino acids is exposed at the virion surface. For LDV, the M protein has been identified as class III membrane protein (5). The M protein is assumed to play an important role in virus assembly and budding. In the ER, it forms disulfide-linked heterodimers (3, 4, 10) with the major glycoprotein GP5 (25–42 kDa), encoded by ORF5. In addition, disulfide-linked M protein homodimers can also be formed, however, they are in general thought not to be incorporated into virions (3).

In another embodiment, the invention provides a particle wherein said first or second structural protein comprises a glycoprotein (GP) or part thereof, such as GP2, GP2b, GP3, GP4 or, preferably, GP5. GP5 is the major glycoprotein of arteriviruses and is suggested to be a class I glycoprotein (5). It contains a signal peptide and after processing the protein consists of a short N-terminal ectodomain, a segment that crosses the membrane three times, and a C-terminal endodomain. In addition, the ectodomain contains N-glycosylation sites (12). Recently, the major neutralisation epitope of LDV was mapped to the putative ectodomain (30 aa) of the ORF5 glycoprotein (8). For EAV, the ectodomain of GP5, which is somewhat larger than with LDV, also contains a neutralization epitope.

Since the cysteine residue in the short N-terminal ectodomain of the M protein is naturally involved in the formation of an intermolecular disulfide bridge with a cysteine residue in the ectodomain of the glycoprotein encoded by ORF5, thereby providing a heterodimer, the invention provides for a close to native chimeric particle wherein said first structural protein comprises GP5 or part thereof and said second structural protein comprises a membrane protein (M) or part thereof. Preferably, the invention provides a PRRSV-like particle for the generation of vaccines against PRRS, thus the invention provides a particle wherein said first Arterivirus comprises porcine reproductive and respiratory syndrome virus (PRRSV). In the detailed description a particle according to the invention is provided wherein said second Arterivirus comprises lactate dehydrogenase-elevating virus (LDV), however, it can also be turned around, in that the GP5, or part thereof, preferred is the above identified ectodomain, is LDV derived and the M, or part thereof, preferred is the above identified ectodomain, is PRRSV derived, as long as the heterodimer ca be established by for example disulfide bridge formation. Of course, other Arteriviruses can be used as first and/or second Arterivirus as explained herein, whereby said second Arterivirus may be of the same genus but of another strain or serotype of said first Arterivirus. For PRRSV, it has also been shown that a disulfide bond between the M protein and the GP5 protein is formed (10). This cysteine residue of the M protein is highly conserved between all arteriviruses. For LDV, it has been shown that virions, after treatment with 5–10 mM DTT to disrupt disulfide bonds, lost their infectivity (4). For EAV, the same results were observed (3).

The invention also provides nucleic acid encoding at least a first structural protein derived from a first Arterivirus and a second structural protein wherein said second structural protein is at least partly not derived from said first Arterivirus wherein said first and second structural protein allow for incorporation in an Arterivirus-like particle. Such nucleic acid or transcripts thereof as provided herein allow the production in a host cell, such as a BHK-21 cell, or a macrophage, of a particle according to the invention. Particles according to the invention provided with a nucleic acid according to the invention are herewith also provided, see for example tables 2 and 3 wherein infection of macrophages with chimeric particles as provided herein is shown.

The invention also provides a vaccine comprising such a particle, nucleic acid, or host cell according to the invention. For the purpose of vaccine development, the invention provides a method for attenuation of the virus and one of the accomplishments is reduced viral infectivity. In particular a method is provided obtaining an attenuated Arterivirus (a vaccine) comprising a first Arterivirus with a structural protein that is at least partly not derived from said first Arterivirus, preferably, although not necessarily, as shown herein above, a method wherein said structural protein is at least partly derived from a second Arterivirus, such as wherein said structural protein comprises a heterodimer with another structural protein. When one of said structural proteins comprises a membrane protein (M) or part thereof such dimerisation is particularly useful, at least in those case wherein another one of said structural proteins comprises a glycoprotein, such as GP5, or part thereof.

This is done by reducing the stability of the interaction between the M protein and the GP5 protein, thereby reducing infectivity. In particular, we have determined that the first cysteine residue (in PRRSV at position 8, see FIG. 1) of the ectodomain of the M protein of Arterivirus is essential for the viral life cycle, since no infectious virus was produced from mutants lacking this cysteine. This residue is essential for the disulfide bond between the M protein and GP5 and heterodimerisation between these two structural proteins is essential either for proper virus assembly or for virus entry for example by the interaction of the virus with a receptor. Therefore, we show that the cysteine residue at position 8 (or a similar position relative to the position shown herein for PRRSV) of the ectodomain of the M protein is essential to maintain full infectivity. For this purpose, we substituted this cysteine residue by a serine residue and secondly, we deleted this residue, both by using the infectious cDNA clone of PRRSV (13). RNA transcripts of these so-called mutant full-length cDNA constructs were tested on their ability to express the viral proteins after transfection into BHK-21 cells, and on their ability to generate infectious virus. In addition, several other mutations of the ectodomain of the M protein were introduced in the infectious cDNA clone of LV, including the exchange of the ectodomain of LV by that of LDV, a related arterivirus (FIG. 1) As can be seen from for example tables 2 and 3, wild-type or parent particles can be differentiated from chimeric particles by comparing distinct patterns of reactivity with antibodies; likewise animals infected with field virus can be differentiated from animals vaccinated with such chimeric particles can be differentiated with diagnostic tests utilising such distinct patterns of reactivity. Suitable antigen for such a diagnostic test would be an antigenic part of the wild-type virus that is not or only partly present in the vaccine. For example, for the vaccines described in the detailed description, an 16–18 amino acid stretch, or antigenic parts thereof of the ectodomain of M can be used, in combination with antibodies having similar specificity as Mabs 126.3 or 126.4. The invention thus also provides a method for controlling or eradicating an Arterivirus infection in a population of animals comprising testing samples (e.g. bloodsamples) of animals vaccinated with a vaccine according to the invention for the presence or absence of antibodies differentiating such animals from animals infected with a wild-type Arterivirus, e.g. by applying routine cull and control measures.

The invention is further explained in the detailed description herein without limiting the invention.

LEGENDS

FIG. 1. Comparison of the amino acid sequences of the M proteins of the arteriviruses EAV, LDV-P, PRRSV-Ter Huurne, PRRSV-VR2332, and SHFV.

FIG. 2 GP5-Mprotein costructs

FIG. 3 Growth curves of deletion mutants

DETAILED DESCRIPTION

Materials & Methods

Cells and Viruses.

BHK-21 cells were grown in BHK-21 medium (Gibco BRL), completed with 5% FBS, 10% tryptose phosphate broth (Gibco BRL), 20 mM Hepes pH 7.4 (Gibco BRL) and 200 mM glutamine, 10 U/ml penicillin and 10 μg/ml streptomycin. Porcine alveolar lung macrophages (PAMs) were maintained in MCA-RPMI-1640 medium, containing 10% FBS, 100 μg/ml kanamycin, 50 U/ml penicillin and 50 μg/ml streptomycin. Virus stocks were produced by serial passage of recombinant LV viruses secreted in the culture supernatant of tranfected BHK-21 cells on PAMs. Virus was harvested when PAMs displayed cytopathic effect (cpe) usually 48 hours after infection. Virus titers (expressed as 50% tissue culture infective doses [TCID50] per ml) were determined on PAMs using end point dilution (19).

Construction of Mutations in the Ectodomain of the M Protein of PRRSV.

PCR-mutagenesis was used to mutate amino acids of the ectodomain of the M protein in the PacI-mutant of the genome-length cDNA clone of LV (pABV437) (13). The primers used are listed in Table 1. The PCR fragments were digested with StuI and HpaI and ligated into these sites of pABV651, a subclone of pABV437 containing the region encoding the structural proteins of PRRSV. Standard cloning procedures were performed essentially as described by (17). Transformation conditions were used as described by Sambrook et al. (17). Sequence analysis was performed to confirm the inserted mutations. Clones containing the correct inserts were digested with AatII and HpaI and ligated into the appropriate sites of pABV437.

First, the cysteine residue at position 8 in the ectodomain of the M protein was substituted by a serine residue by PCR-mutagenesis with primers LV217 and LV93, resulting in subclone pABV702 and full-length clone pABV705. In addition, this cysteine residue was deleted from the ectodomain of M by PCR-directed mutagenesis with primers LV227 and LV93. This resulted in subclone pABV703 and full-length cDNA clone pABV706. Second, the complete ectodomain of the M protein (amino acids 1 to 16) was replaced by the ectodomain of LDV using primers LV218 and LV93. The designed clones were named pABV704 (subclone) and pABV707 (full-length cDNA clone). Third, several other amino acid substitutions and deletions in the ectodomain of ORF6 were created, using LV 219 to LV226 as forward primers and LV93 as reversed primer, resulting in subclones pABV732 till pABV736 and full-length cDNA clones pABV737 till pAB743.

Sequence Analysis.

The regions of the subclones originating from the PCR products were analyzed by nucleotide sequencing. Sequences were determined with the PRISM Ready Dye Deoxy Terminator cycle sequencing kit and the ABI PRISM 310 Genetic Analyzer (Perkin Elmer).

In vitro Transcription and Transfection of BHK-21 Cells.

The constructed full-length genomic cDNA clones and derivatives thereof were linearized with PvuI and in vitro transcribed using T7 RNA polymerase (9). BHK-21 cells were transfected with the resulting RNA by electroporation as described before (13). The medium was harvested 24 h after transfection, and BHK-21 cells were washed with PBS, dried and stored at −20° C. until the IPMA was performed.

Infection of PAMs

To rescue infectious virus, the culture supernatant of BHK-21 cells was harvested 24 hours after transfection and used to inoculate PAMs. After 1 hour the inoculum was removed and fresh culture medium was added. Approximately 24 hours after infection the culture supernatant was harvested and PAMs were washed with PBS, dried and stored at −20° C. until the immuno peroxidase monolayer assay was performed.

Immuno Peroxidase Monolayer Assay (IPMA).

Immunostaining of BHK-21 cells and PAMs was performed by the methods described by Wensvoort et al. (19), in order to determine transient expression and infectious virus, respectively. A panel of monoclonal antibodies (MAbs) (126.3, 126.4, 122.9, 126.12, 126.6 (18)) directed to unknown antigenic sites of the M protein were used to study the expression of the M protein and the presence of antigenic sites thereon. MAbs 122.14, 122.1, and 122.17 (18) (directed against GP3, GP4, and the N protein respectively), were used to detect the expression of other PRRSV proteins.

Analysis of the Production of Non-infectious Virus of the Recombinant RNA Transcripts.

From the culture supernatant of transfected BHK-21 cells, viral RNA was isolated to determine whether the full-length cDNA recombinants were packaged into viruses or virus-like particles, which were non-infectious. A volume of 500 μl proteinase K buffer (100 mM Tris-HCl [pH 7.2], 25 mM EDTA, 300 mM NaCl, 2% [wt/vol] sodium dodecyl sulfate) and 0.2 mg Proteinase K was added to 500 μl supernatant. After incubation for 30 minutes at 37° C., the RNA was extracted with phenol-chloroform and precipitated with ethanol. The RNA was reverse transcribed with primer LV76. Then, PCR was performed with primers LV35 and LV7 to amplify fragments comprising the region in which the mutations were introduced. Sequence analysis was performed to determine whether the mutations introduced in the cDNA clone were also present in the isolated viral RNA.

Radio Immuno Precipitation (RIP).

The expression of GP5 and the M protein were analyzed by metabolic labeling of transfected BHK-21 cells, followed by immunoprecipitation using peptide sera or MAbs directed against GP5 or the M protein, respectively, essentially as described by Meulenberg et al [Meulenberg, 1996

#10]. In addition, the co-precipitation of both proteins was investigated by lyzing the cells under non-reducing conditions. The samples were analyzed by sodium dodecyl sulfate polyacrylamide gel electrophoresis (SDS-PAGE) using a 14% denaturing acrylamide gel.

Results

In order to test whether the disulfide bond between the ectodomains of GP5 and the M protein of PRRSV is essential for viral infection, we substituted amino acid residue 8 of the M protein (10), by a serine residue. In addition, this cysteine residue was deleted from the ectodomain of the M protein. The cysteine substitution and deletion mutations were subsequently introduced in the infectious clone pABV437 of the Lelystad virus isolate of PRRSV, resulting in plasmids pABV705 (C->S) and pABV706 (C->deletion). The RNA transcripts of these full-length cDNA clones were transfected into BHK-21 cells and the expression of the viral proteins was examined. In both cases, the cells stained positive in IPMA with the GP3, GP4, and N specific MAbs (table 2). In addition, MAb 126.12 directed against the M protein resulted in positive staining. Two other MAbs directed against the M protein, 126.3 and 126.4, stained BHK-21 cells transfected with transcripts from pABV705, but not those transfected with transcripts from pABV706 (table 2). This indicated that these MAbs were directed against the ectodomain of the M protein, or at least directed against (a) peptide fragment(s) comprising some of the 18 amino acids comprising said domain. The supernatants of the transfected cells were used to infect PAMs to rescue infectious virus. However, no staining of any of the MAbs could be detected on PAMs 24 hours after transfection (table 3). In addition, no cytopathogenic effect (cpe) could be induced. In conclusion, full-length cDNA transcripts of PRRSV lacking the cysteine residue at position 8 of the M protein, either by substitution or deletion, were able to replicate and express the viral proteins in BHK-21 cells, but unable to produce infectious virus.

Second, the ectodomain of the M protein was exchanged by the ectodomain of LDV, resulting in the full-length cDNA clone pABV707. BHK-21 cells transfected with transcripts from this PRRS recombinant could be stained with MAbs against GP3, GP4, and the N protein, MAb 126.12 directed against the M protein, but not with the MAbs 126.3 and 126.4 (table 2). This confirmed the above described results, that these MAbs reacted with the ectodomain of the M protein. To test the production of infectious chimeric virus, PAMs were infected with the supernatant of the transfected BHK-21 cells. In IPMA, PAMs could be stained with all but MAbs 126.3 and 126.4 (table 3). In conclusion, the ectodomain of the M protein can be replaced by the ectodomain of LDV, resulting in the production of a chimeric virus, which still infects porcine alveolar macrophages. Studies on coronaviruses suggest that all domains of the M protein are important for coronavirus assembly (1). The amino-terminal domain of the M protein, which is exposed on the outside of the virus, plays a role in virus assembly. In addition, the carboxy-terminal domain, located inside the virus envelope, is also important for virus assembly by interacting with the nucleocapsid. This domain is also crucial for the assembly of the viral envelope. However, they showed that the amino-terminal domain of the M protein was not involved in the interaction between the M protein and the S protein (2). This indicates that the association between the proteins takes place at the level of the membrane, possibly also involving part of the M proteins carboxy-terminal domain. For another coronavirus, TGEV, MAbs against the carboxyterminus of the M protein have been described to neutralise virus infectivity (16), indicating that the C-terminal domain of the M protein is exposed on the outside of the virus particle. This topology of the M protein probably coexists with the structure currently described for the M protein of coronaviruses, which consists of an exposed amino terminus and an intravirion carboxy-terminal domain. In our recent study, we are mutating other amino acids in the ectodomain of the M protein. We show that distinct deletions or mutations result in a weakening of the disulfide bond between the M protein and GP5. These constructs show in general normal replication and expression of the structural proteins, resulting in an immune response comparable to wild type. However, fewer virus particles will be produced. Also it results in the production of virus particles, which are impaired in the infection of the macrophage. In both cases, it results in a virus, which is considered to be a safe vaccine for protection of pigs against for example PRRSV. Our results also showed that mutations in the ectodomain of the M protein can result in the generation of a marker vaccine, since replacement with the LDV ectodomain, as well as deletion of some of its amino acids, such as the deletion of the cysteine residue resulted in the loss of the binding of two MAbs. So mutation of the virus at this epitope results in the generation of a marker vaccine. In this study we also showed that PRRSV transcripts containing the ectodomain of the M protein of LDV, generated an infectious, chimeric virus, also useful as a (marker) vaccine.

Materials and Methods

Further Construction of Mutations in the Ectodomain of the M Protein of PRRSV.

First, the cysteine residues at position 50, 111, and 117 in GP5 were substituted by serine residues. For subsitution of amino acid 50, PCR-mutagenesis was performed with primers LV32 and LV303 for the first fragment and with primers LV302 and LV182 for the second fragment. For subsitution of amino acid 111, PCR-mutagenesis was performed with primers LV32 and LV311 for the first fragment and with primers LV310 and LV182 for the second fragment. For subsitution of amino acid 117, PCR-mutagenesis was performed with primers LV32 and LV313 for the first fragment and with primers LV312 and LV182 for the second fragment. The fragments were fused and amplified using the most 5' and 3' primers. The resulting fragments were cloned using BstXI and NheI in pABV651, and from the resulting clones, the AatII-HpaI fragment was cloned into the appropriate sites of pABV437. This resulted in pABV858, 861, and 859 for the cysteine residues 50, 111, and 117, respectively.

Second, the region from amino acid 9 till 16 was deleted from the ectodomain of the M protein. PCR was performed using primers LV32 and LV306. The fragment was digested with BstXI-NheI and cloned into these sites of pABV651. From this clone, the AatII-HpaI fragment was cloned into the corresponding sites of pABV437, resulting in pABV855.

Third, the region encoding the ectodomain of the M protein of LV was substituted by that of other arteriviruses. For introduction of the VR2332 ectodomain, two sequential PCRs were performed with primers LV32 and PRRSV57 and with primers LV32 and PRRSV58. Cloning of the PCR fragment with BstXI and NheI into pABV651 and from this resulting clone with AatII and HpaI into pABV437 resulted in the full-length clone pABV857. For introduction of the ectodomain of M of EAV, we performed sequential PCRs with primers LV32 and PRRSV59 and with primers LV32 and PRRSV60. The resulting fragment was cloned with BstXI and NheI into pABV651, and from the resulting clone with AatII and HpaI into pABV437, resulting in pABV856.

Forth, the overlap between LV ORF5 and 6 was removed by performing PCR with primers LV32 and LV358. The resulting PCR fragment was cloned into the BstXI and StuI sites of pABV651. From the resulting clone, the AatII-HpaI fragment was introduced into pABV437, resulting in pABV871. In this clone, the ectodomains of other arteriviruses were introduced. For introduction of the ectodomain of the M protein of VR2332, two PCR fragments were generated, one using LV32 and LV357 and one using LV356 and 118U250. For introduction of the ectodomain of the M protein of EAV, PCR fragments were generated with primers LV32 and LV361 and with primers LV360 and 118U250. The PCR fragments were fused and amplified with primers LV32 and 118U250. Both PCR fragments were digested with BstXI and HpaI, and ligated into these sites of pABV651. The resulting clones were digested with AatII and HpaI, and the fragments were ligated into these sites of pABV437. This resulted in clone pABV872 for the ectodomain of the M protein of VR2332 and in pABV873 for the ectodomain of the M protein of EAV.

The Primers used are Listed in Table 4.

Results

Full-length cDNA Clones Containing Deletions in the Ectodomain of the M Protein.

RNA transcripts of pABV738 (aa 15& 16 deletion), pABV739 (aa 15 deletion), pABV740 (aa 15 Q to E), pABV741 (aa 9 deletion), and pABV742 (aa 5 deletion) were transfected into BHK-21 cells and tested for the expression of the structural proteins 24 hours after transfection in IPMA. For all mutants, expression of GP3, GP4, and N was detected. Two MAbs against the M protein (126.3 and 126.4) did not stain the transfected cells, in contrast to another Mab against the M protein (126.12), which stained the cells positive. The culture supernatant of the transfected cells was used to infect PAMs. Staining 24 hours after infection showed expression of the N protein for all mutants. This indicates that all mutants produced viable virus.

In addition, a mutant in which the coding region for amino acid 9 till 16 from the M protein was deleted was constructed, resulting in pABV855. Transfection of its RNA transcripts into BHK-21 cells showed expression of all the structural proteins of LV. MAbs 126.3 and 126.4, however, did not stain the transfected cells. After inoculation of PAMs with the culture supernatant of the transfected cells, no expression of the structural proteins was detected. In conclusion, no viable virus was produced.

Mutations of Cysteine Residues in the GP5 Protein.

Cysteine residues 50, 111, and 117 of GP5 were changed into serine residues, resulting in the full-length cDNA clones pABV858, pABV 861, and in pABV 859, respectively. Transfection of RNA transcripts in BHK-21 cells showed for all mutants expression of the structural proteins, as detected in IPMA 24 hours after transfection. PAMs were inoculated with the culture supernatant of the transfected cells and stained in IPMA 24 hours after infection. Cells stained positive when PAMs were inoculated with culture supernatant of BHK-21 cells transfected with RNA transcripts of pABV861 and 859, in contrast to PAMs inoculated with culture supernatant of BHK-21 cells transfected with RNA transcripts of pABV858, for which no positive staining was observed. In conclusion, the cysteine residue at position 50 of GP5 is essential for the production of viable virus, and residues 111 and 117 are not.

Introduction of the Ectodomain of the M Protein of Other Arteriviruses.

Since introduction of the ectodomain of the M protein of LDV resulted in the production of viable virus, we now inserted the ectodomain of the M protein of VR2332 and that of EAV into the infectious cDNA clone of LV, resulting in pABV857 and pABV856, respectively (FIG. 2A). However, both introductions of these sequences introduced mutations in the C-terminus of the GP5 protein, since the coding sequences for GP5 and M, ORF5 and 6, respectively, overlap. Transfection of their RNA transcripts showed for both mutants expression of the structural proteins. However, staining of PAMs infected with the culture supernatant of transfected BHK-21 cells was negative. In conclusion, no viable virus is produced from these chimeric arteriviruses.

Removal of the Overlap Between ORF5 and 6 and Introduction of Chimeric Sequences.

Since introduction of the ectodomain of M of VR2332 and EAV also introduced mutations in the region encoding the C-terminus of GP5, we removed the overlap between ORFs5 and 6 from the infectious cDNA clone of LV. In this way, we wanted to create a region in ORF6 at which arterivirus sequences could be introduced without disturbing the coding sequence of ORF5. First, the overlap between ORF5 and 6 was removed in the infectious cDNA clone, resulting in pABV871 (FIG. 2B). Transfection of its RNA transcripts into BHK-21 cells revealed that the structural proteins were expressed, indicating that both replication and transcription were not disturbed. Infection of PAMs with the culture supernatant of transfected BHK-21 cells showed that infectious virus was produced since structural protein expression was detected by IPMA and cpe was observed. Second, the ectodomain of the M protein of VR2332 and that of EAV were introducted in this construct, resulting in pABV872 and pABV873 (FIG. 2B). Their RNA transcripts were transfected into BHK-21 cells. All, but 126.3 and 126.4, MAbs stained the transfected cells positive. PAMs infected with the culture supernatant of transfected BHK-21 cells showed expression of all structural proteins in IPMA. These results indicate that the ectodomain of the M protein of other arteriviruses, providing that the C-terminus of the GP5 was left intact, could be functionally exchanged by that of the ectodomain of the LV M protein.

Genetic Stability of Chimeric Arteriviruses.

In order to investigate whether the viruses generated from pABV707, 738, 741, and 742, 871, 872 and pABV873 were stably maintained in vitro, they were serially passaged on PAMs. The viral RNA was isolated from the culture supernatant after 5 passages, and studied by genetic analysis. The viral RNA was reversely transcribed and the region flanking the introduced deletions was amplified by PCR. Sequence analysis of the fragment showed that for each mutant the introduced mutations were still present and that no additional mutations had been introduced in the flanking regions during in vitro passages. These results indicate that the deletions were maintained stably during in vitro passaging on PAMs.

Growth characteristics were determined for vABV707, vABV741, and vABV742 in a growth curve and compared with those of wild type vABV437. PAMs were infected with passage 5 at a multiplicity of infection of 0.05, and the culture medium was harvested at various time intervals. Virus titers were determined by end point dilution on macrophages. In all cases, we observed that the growth rates were similar, however, the amount of viable virus inclined faster after reaching its highest titer. This result might indicate that the generated viruses are thermolabile which may be a further useful property for vaccine purposes.

TABLE 3

Staining of PAMs infected with supernatant of transfected BHK-21 cells with pABV437, 705, 706, and 707.

| pABV | M (126.3) | N (122.17) |
|---|---|---|
| 437 | + | + |
| 705 | – | – |
| 706 | – | – |
| 707 | + | + |

+: positive staining
–: no staining

TABLE 1

Primers used in PCR-mutagenesis and sequencing

| Primer (nt.) | Sequence of primer[a] | Primer Orientation/ location | Purpose |
|---|---|---|---|
| 39U247 | 5' GCCAAGGCAACACAATCTGC 3' | – 14368 | Sequencing |
| LV7 | 5' AATGTAAAGGAAGAGCTCAGAA 3' | – 14222 | PCR on RT-PCR viral |
| LV8 | 5' ACTTTATCATTGGATCGAGCA 3' | – 14673 | RNA |
| LV17 | 5' CCCTTGACGAGCTCTTCGGC 3' | + 14045 | Sequencing |
| LV35 | 5' GATTACGCGTGCTGCTAAAAATTGC 3' | + 13867 | Sequencing |
| LV76 | 5' TCTAGGAATTCTAGACGATCG$(T)_{40}$ 3' | – 15088 | PCR on |
| LV93 | 5' ACTTTATCATTGGATCCAGCA-3' | – 14581 | RT-CR on RT-PCR |
| LV198 | 5' TTTTCCGGGCATACTTGAC 3' | + 14086 | Viral RNA |
| LV217 | 5' AATGGGAGGCCTAGACGATTTTTCCAACGA 3' | + 14086 | Reverse primer cloning |
| LV218 | 5' | + 14086 | Sequencing |
| LV219 | AATGGGAGGCCTAGAA*TTTTGTGATCAAACTTCCTGGTATCA* | + 14086 | M protein a.a. 8 C to S |
| LV220 | GCTCGTGCTAGCG 3' | + 14086 | M protein a.a. 1–16 LV |
| LV221 | 5' | + 14086 | to LDV |
| LV222 | AATGGGAGGCCTAGACGATTTTTTGCAACGATCCTATCGCCGC | + 14086 | M protein a.a. 16 K |
| LV225 | ACAACTCGTGCTA 3' | + 14086 | deletion |
| LV226 | 5' | + 14086 | M protein a.a. 15/16 |
| LV227 | AATGGGAGGCCTAGACGATTTTTGCAACGATCCTATCGCCGC | + 14086 | QK deletion |
| | ACTCGTGCTA 3' | | M protein a.a. 9 N |
| | 5' AATGGGAGGCCTAGACGATTTTTGCGATCCTATCGCC 3' | | deletion |
| | 5' AATGGGAGGCCTAGATTTTTTGCAAC 3' | | M protein a.a. 9 N |
| | 5' | | deletion |
| | AATGGGAGGCCTAGACGATTTTTGCAACGATCCTATCGCCGC | | M protein a.a. 15 Q |
| | AAAGCTCGTG 3' | | deletion |
| | 5' | | M protein a.a. 15 Q to |
| | AATGGGAGGCCTAGACGATTTTTGCAACGATCCTATCGCCGC | | E |
| | AGAAAAGCTC 3' | | M protein aa. 8 C→ |
| | 5' AATGGGAGGCCTAGACGATTTTAACGATCCT | | deletion |

[a]Restriction sites are underlined, foreign sequences are in italic

TABLE 2

Staining of BHK-21 transfected with transcripts from pABV437, 705, 706, and 707.

| pABV | GP3 (122.14) | GP4 (122.1) | M (126.3) | M (126.4) | M (126.12) | N (122.17) |
|---|---|---|---|---|---|---|
| 437 | + | + | + | + | + | + |
| 705 | + | + | + | + | + | + |
| 706 | + | + | – | – | + | + |
| 707 | + | + | – | – | + | + |

+: positive staining
–: no staining

TABLE 4

Sequences of the primers used to introduce deletions by PCR, and primers used to sequence the introduced mutations.

| Primer | Sequence of the primer[a] | Orientation | Purpose (pABV) | Location |
|---|---|---|---|---|
| 39U247 | 5' GCCAAGGCAACACAATCTGC 3' | − | sequencing | 14368 |
| 118U250 | 5' CAGCCAGGGGAAAATGTGGC 3' | − | sequencing/PCR | 14745 |
| LV17 | 5' CCCTTGACGAGCTCTTCGGC 3' | + | sequencing/PCR | 14045 |
| LV32 | 5' GATTGGATCCATTCTCTTGGCAATATG 3' | + | sequencing/PCR | 13466 |
| LV75 | 5' TCTAGGAATTCTAGACGATCG 3' | − | PCR | 15088 |
| LV76 | 5' TCTAGGAATTCTAGACGATCG(T)$_{40}$ 3' | − | RT-PCR | 15088 |
| LV93 | 5' ACTTTATCATTGGATCCAGCA 3' | − | PCR | 14581 |
| LV182 | 5' GGATTGAAAATGCAATTAATTAATCATGTAT 3' | − | PCR | 14257 |
| LV198 | 5' TTTTCCCGGGCATACTTGAC 3' | + | Sequencing | 14086 |
| PRRSV57 | 5' *TGCTATCATGACAGAAGTCATCTAAGGACGACCCCAT*TGCTCAG 3' | − | 857 | 14132 |
| PRRSV58 | 5' GCTAAAG<u>GCTAGC</u>ACGAGC*TTTTGTGGAGCCGTGCTATCATGAC* 3' | − | 857 | 14132 |
| PRRSV59 | 5' *ATCCCGTCACCACAAAATGAATCTATGGCTCCCAT*TGGTCAG 3' | − | 856 | 14132 |
| PRRSV60 | 5' GCTAAAG<u>GCTAGC</u>ACGAGC*TCACCTAAAATCCCGTCACCA* 3' | − | 856 | 14132 |
| LV302 | 5' CTTGACGATA*TCA*GAGCTGAATGGG 3' | + | 858 | 13630 |
| LV303 | 5' CCCATTCAGCTCTGATATCGTCAAG 3' | − | 858 | 13630 |
| LV306 | 5' GCTAAG<u>GCTAGC</u>ACGAGGCAAAAATCGTC 3' | − | 855 | 14132 |
| LV310 | 5' GTACGTACTC*TCA*AGCGTC 3' | + | 861 | 13814 |
| LV311 | 5' GACGCT*TGA*GAGTACGTAC 3' | − | 861 | 13814 |
| LV312 | 5' CTACGGCGCT*TCA*GCTTTCG 3' | + | 859 | 13832 |
| LV313 | 5' CGAAAGC*TGA*AGCGCGGTAG 3' | − | 859 | 13832 |
| LV356 | 5' GCAGTGGGAGGCCTGATG*GGGTCGTCCTTAG* 3' | + | 872 | 14083 |
| LV357 | 5' *CTAAGGACGACCCC*ATCAGGCCTCCCACTGC 3' | − | 872 | 14083 |
| LV358 | 5' CGTCTAGGCCTCCCATCAAGCTTCCCACTGC 3' | − | 871 | 14083 |
| LV360 | 5' GCAGTGGGAGGCCTGATGGGAGCCATAGATTC 3' | + | 873 | 14083 |
| LV361 | 5' *GAATCTATGGCTCCC*ATCAGGCCTCCCACTGC 3' | − | 873 | 14083 |

[a]The restriction sites are underlined, foreign sequences are in italic

VACCINATION EXAMPLES

Intranasal Inoculation of Wild-type PRRSV (EU en US-type) After Vaccination of 8-week Old Pigs with Specified PRRSV-mutants; Virus Kinetics and Antibody Response Introduction The Porcine Reproductive and Respiratory Syndrome Virus (PRRSV) causes abortion and poor litter quality in third trimester pregnant sows. Moreover, it may cause respiratory disease in young pigs. Infection of late term pregnant sows (80–95 days) with PRRSV can cause profound reproductive failure, especially due to a high level of mortality among the off-spring of these sows at birth and during the first week after birth. PRRSV is a ubiquitous pathogen. Two distinct antigenic types can be distinguished, i.e. the European and the American type. Clinical effects after a PRRSV infection depend on the type of strain involved. Vaccination of pigs with a PRRS vaccine influences the way a PRRSV-challenge works out on an animal and a farm level. The level and duration of viraemia, and shedding of the field-virus is reduced by this vaccination.

For the development of a second generation PRRS vaccine, new candidates are to be tested. Therefore, 8-week old pigs were vaccinated with a number of specified PRRSV-mutants (recombinant viruses), after which a PRRSV-challenge was given. Kinetics of this virus exposure is scored in terms of level and duration of viremia and booster responses, both in a homologous and heterologous set-up.

Aims of the Study

The determination of the immunological efficacy and safety of defined PRRSV-mutants used as a vaccine in a vaccination-(homologous and heterologous) challenge model. Along with this, mutant immunogenicity was tested.

Study Design

Four PRRSV mutants were tested which all full-filled the following criteria:
  genetic stability after 5 passages in-vitro (cell cultures)
  genetic stability after 3 weeks of exposure to animals
  immunogenicity (as determined by IDEXX elisa)
The following mutants were tested:
vABV707: LDV-PRRS chimeric virus (ectodomain of M exchange)
vABV741: aa9 deletion of the M-protein of PRRSV
vABV746: 18 nucleotide deletions at the C-terminal part of ORF7
vABV688: mutations at position 88–95 of ORF2

As a positive control, the following virus was used:
vABV437: wild-type recombinant of Lelystad virus Each Mutant was Tested in Two Groups Each Consisting of 5 SPF-pigs of 8 Weeks Old.

All groups were completely segregated without any contact with each other. Two naive sentinel pigs (so, one per each mutant-group) were united with these vaccinated pigs 24 hours after vaccination and removed and killed 28 days thereafter.

In the 2 groups (per mutant) each consisting of 5 vaccinates, two animals were challenged with wild-type virus (i.e. Lelystad virus (LV-tH) as a representative of an European strain of PRRSV or SDSU#73 as a representative of an American (US) strain of PRRSV), at day 28 post-vaccination.

The other three vaccinates were separated from these challenged animals for 24 hours and re-united thereafter. 28 days after challenge, all pigs were removed and destroyed.

vABV437 served as a positive control. A challenge control was included for 14 days starting at the moment of challenge in order to control challenge efficacy with LV-tH and SDSU#73, Animals were treated as described for the other animals during the challenge phase.

The allocation of the pigs is outlined in Table 1.

TABLE 1

Allocation of pigs to designated groups. Each mutant group consisted of 5 vaccinated pigs and 1 sentinel (*so each PRRSV-mutant had two groups). Groups 11 and 12 served as challenge control groups (**) consisting of 5 animals per group; only two of these pigs were intranasally exposed to LV-tH or SDSU#73. All mutant groups were housed in isolation recombinant facilities, whereas the wild-type groups were housed in standard isolation facilities.

| Group | Challenge | Vaccination | N animals | Stables |
|---|---|---|---|---|
| 1 + 2 | LV-tH/ SDSU#73 | 707 | 12* | 2 (geb. 46) |
| 3 + 4 | LV-tH/ SDSU#73 | 741 | 12* | 2 (HRW-223.030/40) |
| 5 + 6 | LV-tH/ SDSU#73 | 746 | 12* | 2 (HRW-223.050/60) |
| 7 + 8 | LV-tH/ SDSU#73 | 688 | 12* | 2 (HRW-223.070/80) |
| 9 + 10 | LV-tH/ SDSU#73 | 437 | 12* | 2 (EHW) |
| 11 + 12 | LV-tH/ SDSU#73 | — | 10** | 2 (EHW) |

The vaccines were administered intramuscularly according to a SOP (2 ml deep intramuscularly in the neck halfway between the shoulder and the right ear; min titer $10^5$ $TCID_{50}$/ml). All inoculae were titrated before and after usage and were stored on melting ice at all times.

Experimental Animals

70 SPF pigs of 8-weeks old, tested free of PRRSV.

Execution of the Study (Table 2)

TABLE 2

Course of the study valid for each of the mutant groups.

| Day | Action |
|---|---|
| −5 till 0 | Acclimatisation of animals |
| −2 | Serum sampling for IDEXX-ELISA |
| Daily | General clinical status |
| 0 | Vaccination of 5 animals per group (2 ml intramuscular) |
| 1 | Sentinels |
| 3 × per week sampling | Serum sampling for virus isolation (3 × per week) and INDEXX-ELISA (1 × week) |
| Dag 28 | Removal of sentinels and challenge of 2 vaccinates with LV-tH or US virus (in stable 1 and 2 per mutant group, respectively) |
| 3 × per week sampling | Serum sampling for virus isolation (3 × per week) and INDEXX-ELISA (1 × week) |
| 56 | Finalization; destruction of pigs |

Results

No adverse reactions were noted after exposure of the mutant virus or wild-type viruses to the pigs in each of the groups.

Tables 3 and 4 show the results of the PRRS virus isolation from serum and calculated viraemia scores. Incidences of viraemia at defined sampling points were determined by virus isolation on porcine alveolar macrophages using routine and published techniques;

Virus positivity at a serum sample dilution of 1:10 was designated (+), and (++) means virus positivity at a serum sample dilution of 1:100. These results were used to calculate a group total "viraemia score" as (type 1) the percentage of the virus-exposed animals in each group (each virus positive animal at each time-point=1 point, so a max score of 100% (=12/12) can be obtained, and (type 2) as the percentage of maximal viraemia of the exposed animals. In the latter case, a max score of 100% (=24/24) can be obtained based upon the fact that max viraemia is scored as 2 points (1:100 dilution of the samples) for each individual animal. All mutant virus groups showed a reduced type 1 and type 2 viremia score as compared to vABV437. vABV707 vaccinated pigs showed a reduced type 1 and type 2 viraemia score prior to challenge as compared to the score of the pigs in all other groups. At the moment of challenge no animals were shown to be viraemic any more. All sentinels became viraemic and sero-converted, meaning that the viruses shedded from the exposed pigs to the sentinels. It is shown that primary exposure of the mutant viruses to the pigs renders an effective immunological response as determined by a near complete prevention of viraemia after homologous wild-type challenge and a firm reduction of viraemia after heteroogous challenge as compared to challenge controls. Vaccinated sentinels were effectively protected.

No differences could be documented in serological responses after vaccination and challenge between each of the groups studied.

Challenge controls all show viraemia during the course of the 14-day study, where the viraemia is most predominant in the intranasally exposed pigs.

TABLE 3

Type 1 viraemia score. A group total "viraemia score" was calculated as the percentage of the virus-exposed animals in each group. Each virus positive animal at each time-point = 1 point, so a max score of 100% (=12/12) can be obtained.

| dpi | vABV707 | vABV741 | vABV746 | vABV688 | vABV437 | Wild-type |
|---|---|---|---|---|---|---|
| 0 | 0, 0 | 0, 0 | 0, 0 | 0, 0 | 0, 0 | |
| 2 | 0, 0 | 8, 3 | 25, 0 | 16, 7 | 75, 0 | |
| 4 | 16, 7 | 83, 3 | 91, 7 | 75, 0 | 100, 0 | |
| 7 | 91, 7 | 83, 3 | 91, 7 | 100, 0 | 100, 0 | |
| 9 | 91, 7 | 91, 7 | 91, 7 | 83, 3 | 100, 0 | |
| 11 | 50, 0 | 100, 0 | 66, 7 | 100, 0 | 100, 0 | |
| 14 | 66, 7 | 83, 3 | 83, 3 | 83, 3 | 100, 0 | |
| 16 | 33, 3 | 58, 3 | 58, 3 | 66, 7 | 75, 0 | |
| 18 | 41, 7 | 16, 7 | 25, 0 | 33, 3 | 50, 0 | |
| 21 | 25, 0 | 8, 3 | 33, 3 | 16, 7 | 91, 7 | |
| 23 | 25, 0 | 16, 7 | 25, 0 | 0, 0 | 41, 7 | |
| 25 | 8, 3. | 0, 0 | 0, 0 | 16, 7 | 16, 7 | |
| 28 | 0, 0 | 0,0 | 0, 0 | 0, 0 | 0, 0 | 0 |
| 30 | 10, 0 | 0,0 | 30, 0 | 30, 0 | 10, 0 | 0 |
| 32 | 20, 0 | 0, 0 | 10, 0 | 20, 0 | 40, 0 | 40 |
| 35 | 20, 0 | 10, 0 | 10, 0 | 20, 0 | 20, 0 | 60 |
| 37 | 0, 0 | 30, 0 | 0, 0 | 20, 0 | 20, 0 | 90 |
| 39 | 10, 0 | 0, 0 | 0, 0 | 0, 0 | 30, 0 | 90 |
| 42 | 0, 0 | 0, 0 | 0, 0 | 0, 0 | 10, 0 | 100 |
| 44 | 0, 0 | 0, 0 | 0, 0 | 0, 0 | 0, 0 | |
| 46 | 0, 0 | 0, 0 | 0, 0 | 0, 0 | 0, 0 | |
| 49 | 0, 0 | 0, 0 | 0, 0 | 0, 0 | 0, 0 | |

TABLE 3-continued

Type 1 viraemia score. A group total "viraemia score" was calculated as the percentage of the virus-exposed animals in each group. Each virus positive animal at each time-point = 1 point, so a max score of 100% (=12/12) can be obtained.

| dpi | vABV707 | vABV741 | vABV746 | vABV688 | vABV437 | Wild-type |
|---|---|---|---|---|---|---|
| 51 | 0, 0 | 0, 0 | 0, 0 | 0, 0 | 0, 0 | |
| 53 | 0, 0 | 0, 0 | 0, 0 | 0, 0 | 0, 0 | |
| 56 | 0, 0 | 0, 0 | 0, 0 | 0, 0 | 0, 0 | |

TABLE 4

Type 2 viraemia score, calculated as the percentage of maximal viraemia of the exposed animals. A max score of 100% (=24/24) can be obtained based upon the fact that max viraemia is scored as 2 points (1:100 dilution of the samples) for each individual animal at each time point.

| dpi | vABV707 | vABV741 | vABV746 | vABV688 | vABV437 | Wild-type |
|---|---|---|---|---|---|---|
| 0 | 0, 0 | 0, 0 | 0, 0 | 0, 0 | 0, 0 | |
| 2 | 0, 0 | 4, 2 | 12, 5 | 8, 3 | 37, 5 | |
| 4 | 8, 3 | 50, 0 | 54, 2 | 50, 0 | 70, 8 | |
| 7 | 45, 8 | 58, 3 | 62, 5 | 66, 7 | 83, 3 | |
| 9 | 54, 2 | 50, 0 | 45, 8 | 50, 0 | 58, 3 | |
| 11 | 25, 0 | 70, 8 | 37, 5 | 54, 2 | 95, 8 | |
| 14 | 33, 3 | 62, 5 | 41, 7 | 45, 8 | 70, 8 | |
| 16 | 16, 7 | 45, 8 | 33, 3 | 33, 3 | 41, 7 | |
| 18 | 20, 8 | 8, 3 | 12, 5 | 16, 7 | 37, 5 | |
| 21 | 12, 5 | 8, 3 | 16, 7 | 8, 3 | 50, 0 | |
| 23 | 12, 5 | 8, 3 | 8, 3 | 0, 0 | 41, 7 | |
| 25 | 4, 2 | 0, 0 | 0, 0 | 8, 3 | 8, 3 | |
| 28 | 0, 0 | 0, 0 | 0, 0 | 0, 0 | 0, 0 | 0 |
| 30 | 5, 0 | 0, 0 | 15, 0 | 15, 0 | 5, 0 | 0 |
| 32 | 10, 0 | 0, 0 | 5, 0 | 10, 0 | 20, 0 | 40 |
| 35 | 10, 0 | 5, 0 | 5, 0 | 10, 0 | 10, 0 | 60 |
| 37 | 0, 0 | 15, 0 | 0, 0 | 10, 0 | 10, 0 | 90 |
| 39 | 5, 0 | 0, 0 | 0, 0 | 0, 0 | 15, 0 | 90 |
| 42 | 0, 0 | 0, 0 | 0, 0 | 0, 0 | 5, 0 | 100 |
| 44 | 0, 0 | 0, 0 | 0, 0 | 0, 0 | 0, 0 | |
| 46 | 0, 0 | 0, 0 | 0, 0 | 0, 0 | 0, 0 | |
| 49 | 0, 0 | 0, 0 | 0, 0 | 0, 0 | 0, 0 | |
| 51 | 0, 0 | 0, 0 | 0, 0 | 0, 0 | 0, 0 | |
| 53 | 0, 0 | 0, 0 | 0, 0 | 0, 0 | 0, 0 | |
| 56 | 0, 0 | 0, 0 | 0, 0 | 0, 0 | 0, 0 | |

Conclusion

The studied recombinant mutant PRRS viruses show a reduced virulence as determined by a reduction of viraemia (length and height) as compared to wild-type (vABv437). All mutants instigate an effective immune response for the protection of pigs against a wild-type field PRRSV. The homologous protection seems to be somewhat more effective than the heterologous one. vABV707 seems to be the most suitable vaccine from among tested viruses.

The humoral response is measurable by a commercial ELISA (IDEXX) in all cases. No adverse reactions are elicited.

REFERENCES 1. de Haan, C. A., L. Kuo, P. S. Masters, H. Vennema, and P. J. Rottier. 1998. Coronavirus particle assembly: primary structure requirements of the membrane protein. J Virol. 72:6838–50.
2. de Haan, C. A., M. Smeets, F. Vernooij, H. Vennema, and P. J. Rottier. 1999. Mapping of the coronavirus membrane protein domains involved in interaction with the spike protein. J Virol. 73:7441–52.
3. de Vries, A. A., S. M. Post, M. J. Raamsman, M. C. Horzinek, and P. J. Rottier. 1995. The two major envelope proteins of equine arteritis virus associate into disulfide-linked heterodimers. J Virol. 69:4668–74.
4. Faaberg, K. S., C. Even, G. A. Palmer, and P. G. Plagemann. 1995. Disulfide bonds between two envelope proteins of lactate dehydrogenase-elevating virus are essential for viral infectivity. J Virol. 69:613–7.
5. Faaberg, K. S., and P. G. Plagemann. 1995. The envelope proteins of lactate dehydrogenase-elevating virus and their membrane topography. Virology. 212:512–25.
6. Godeke, G. J., C. A. de Haan, J. W. Rossen, H. Vennema, and P. J. Rottier. 2000. Assembly of spikes into coronavirus particles is mediated by the carboxy-terminal domain of the spike protein. J Virol. 74:1566–71.
7. Kuo, L., G. J. Godeke, M. J. Raamsman, P. S. Masters, and P. J. Rottier. 2000. Retargeting of coronavirus by substitution of the spike glycoprotein ectodomain: crossing the host cell species barrier. J Virol. 74:1393–406.
8. Li, K., Z. Chen, and P. Plagemann. 1998. The neutralization epitope of lactate dehydrogenase-elevating virus is located on the short ectodomain of the primary envelope glycoprotein. Virology. 242:239–45.
9. Liljestrom, P., and H. Garoff. 1991. A new generation of animal cell expression vectors based on the Semliki Forest virus replicon. Biotechnology N Y. 9:1356–61.
10. Mardassi, H., B. Massie, and S. Dea. 1996. Intracellular synthesis, processing, and transport of proteins encoded by ORFs 5 to 7 of porcine reproductive and respiratory syndrome virus. Virology. 221:98–112.
11. Meulenberg, J. J. M., and A. Petersen den Besten. 1996. Identification and characterization of a sixth structural protein of Lelystad virus: the glycoprotein GP2 encoded by ORF2 is incorporated in virus particles. Virology. 225:44–51.
12. Meulenberg, J. J. M., A. Petersen-Den Besten, E. P. De Kluyver, R. J. M. Moormann, W. M. M. Schaaper, and G. Wensvoort. 1995. Characterization of proteins encoded by ORFs 2 to 7 of Lelystad virus. Virology. 206:155–163.
13. Meulenberg, J. J. M., J. N. A. BosDeRuijter, R. vandeGraaf, G. Wensvoort, and R. J. M. Moormann. 1998. Infectious transcripts from cloned genome-length cDNA of porcine reproductive and respiratory syndrome virus. Journal Of Virology. January 72:380–387.
14. Meulenberg, J. J. M., M. M. Hulst, E. J. De Meijer, P. L. J. M. Moonen, A. Den Besten, E. P. De Kluyver, G. Wensvoort, and R. J. M. Moormann. 1993. Lelystad virus, the causative agent of porcine epidemic abortion and respiratory syndrome (PEARS), is related to LDV and EAV. Virology. 192:62–72.
15. Murtaugh, M. P., M. R. Elam, and L. T. Kakach. 1995. Comparison of the structural protein coding sequences of the VR-2332 and Lelystad virus strains of the PRRS virus. Arch Virol. 140:1451–60.
16. Risco, C., I. M. Anton, C. Sune, A. M. Pedregosa, J. M. Martin Alonso, F. Parra, J. L. Carrascosa, and L. Enjuanes. 1995. Membrane protein molecules of transmissible gastroenteritis coronavirus also expose the carboxy-terminal region on the external surface of the virion. J Virol. 69:5269–77.
17. Sambrook, J., Fritsch, E. F., Maniatis, T. 1989. Molecular cloning: a laboratory manual, 2nd ed. Cold Spring Harbor Laboratory, Cold Spring Harbor, N.Y.

18. van Nieuwstadt, A. P., J. J. Meulenberg, A. van Essen Zanbergen, A. Petersen den Besten, R. J. Bende, R. J. Moormann, and G. Wensvoort. 1996. Proteins encoded by open reading frames 3 and 4 of the genome of Lelystad virus (Arteriviridae) are structural proteins of the virion. J Virol. 70:4767–72.
19. Wensvoort, G., C. Terpstra, J. Boonstra, M. Bloemraad, and D. Van Zaane. 1986. Production of monoclonal antibodies against swine fever virus and their use in laboratory diagnosis. Vet Microbiol. 12:101–8.
20. Wensvoort, G., C. Terpstra, J. M. Pol, E. A. ter Laak, M. Bloemraad, E. P. de Kluyver, C. Kragten, L. van Buiten, A. den Besten, F. Wagenaar, and et al. 1991. Mystery swine disease in The Netherlands: the isolation of Lelystad virus. Vet Q. 13:121–30.

---

What is claimed is:

1. A process for producing an attenuated porcine reproductive and respiratory syndrome virus (PRRSV), said process comprising:

substituting a region of a first PRRSV genome encoding M protein ectodomain with a region of a LDV genome encoding M protein ectodomain to create a substituted PRRSV genome, wherein M protein ectodomain encoded from the substituted PRRSV genome forms a heterodimer with GP5 encoded from the substituted PRRSV genome.

2. A process for producing an attenuated porcine reproductive and respiratory syndrome virus (PRRSV), said process comprising:

removing overlap between ORF5 and ORF6 of a first PRRSV genome; and substituting a region of the first PRRSV genome that encoding M protein ectodomain with a region of a second Arterivirus genome encoding M protein ectodomain to create a substituted PRRSV genome, wherein the second Arterivirus is equine arteritis virus (EAV) or a second PRRSV that is not the same serotype as the PRRSV encoded by the first PRRSV genome, and wherein GP5 encoded from the substituted PRRSV genome comprises an intact C-terminus.

3. The process of claim 2, wherein M protein ectodomain encoded from the substituted PRRSV genome forms a heterodimer with GP5 encoded from the substituted PRRSV genome.

* * * * *

SEQUENCE LISTING

```
<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer
      39U247
<220> FEATURE:
<221> NAME/KEY: misc_feature
<222> LOCATION: (1)..(20)

<400> SEQUENCE: 1

gccaaggcaa cacaatctgc                                                20


<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: primer LV7
<220> FEATURE:
<221> NAME/KEY: misc_feature
<222> LOCATION: (1)..(22)

<400> SEQUENCE: 2

aatgtaaagg aagagctcag aa                                             22


<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer LV8
<220> FEATURE:
<221> NAME/KEY: misc_feature
<222> LOCATION: (1)..(21)

<400> SEQUENCE: 3

actttatcat tggatccagc a                                              21


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer LV17
<220> FEATURE:
<221> NAME/KEY: misc_feature
<222> LOCATION: (1)..(20)

<400> SEQUENCE: 4

cccttgacga gctcttcggc                                                20


<210> SEQ ID NO 5
<211> LENGTH: 25
```

-continued

<212> TYPE: DNA
<213> ORGANISM: Artificial Sequence
<220> FEATURE:
<223> OTHER INFORMATION: Description of Artificial Sequence: primer LV35
<220> FEATURE:
<221> NAME/KEY: misc_feature
<222> LOCATION: (1)..(25)

<400> SEQUENCE: 5
gattacgcgt gctgctaaaa attgc 25

<210> SEQ ID NO 6
<211> LENGTH: 61
<212> TYPE: DNA
<213> ORGANISM: Artificial Sequence
<220> FEATURE:
<223> OTHER INFORMATION: Description of Artificial Sequence: primer LV76
<220> FEATURE:
<221> NAME/KEY: misc_feature
<222> LOCATION: (1)..(61)

<400> SEQUENCE: 6
tctaggaatt ctagacgatc gttttttttt tttttttttt tttttttttt tttttttttt 60
t 61

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer LV93
<220> FEATURE:
<221> NAME/KEY: misc_feature
<222> LOCATION: (1)..(21)

<400> SEQUENCE: 7
actttatcat tggatccagc a 21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer
LV198
<220> FEATURE:
<221> NAME/KEY: misc_feature
<222> LOCATION: (1)..(20)

<400> SEQUENCE: 8
ttttcccggg catacttgac 20

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: primer
LV217
<220> FEATURE:
<221> NAME/KEY: misc_feature
<222> LOCATION: (1)..(30)

<400> SEQUENCE: 9
aatgggaggc ctagacgatt tttccaacga 30

<210> SEQ ID NO 10
<211> LENGTH: 55

-continued

<212> TYPE: DNA
<213> ORGANISM: Artificial Sequence
<220> FEATURE:
<223> OTHER INFORMATION: Description of Artificial Sequence: primer
LV218
<220> FEATURE:
<221> NAME/KEY: misc_feature
<222> LOCATION: (1)..(55)

<400> SEQUENCE: 10
aatgggaggc ctagaatttt gtgatcaaac ttcctggtat cagctcgtgc tagcc 55

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: primer
LV219
<220> FEATURE:
<221> NAME/KEY: misc_feature
<222> LOCATION: (1)..(55)

<400> SEQUENCE: 11
aatgggaggc ctagacgatt tttgcaacga tcctatcgcc gcacaactcg tgcta 55

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: primer
LV220
<220> FEATURE:
<221> NAME/KEY: misc_feature
<222> LOCATION: (1)..(52)

<400> SEQUENCE: 12
aatgggaggc ctagacgatt tttgcaacga tcctatcgcc gcactcgtgc ta 52

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: primer
LV221
<220> FEATURE:
<221> NAME/KEY: misc_feature
<222> LOCATION: (1)..(37)

<400> SEQUENCE: 13
aatgggaggc ctagacgatt tttgcgatcc tatcgcc 37

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: primer
LV222
<220> FEATURE:
<221> NAME/KEY: misc_feature
<222> LOCATION: (1)..(25)

<400> SEQUENCE: 14
aatgggaggc ctagattttt gcaac 25

<210> SEQ ID NO 15

-continued

<211> LENGTH: 52
<212> TYPE: DNA
<213> ORGANISM: Artificial Sequence
<220> FEATURE:
<223> OTHER INFORMATION: Description of Artificial Sequence: primer
      LV225
<220> FEATURE:
<221> NAME/KEY: misc_feature
<222> LOCATION: (1)..(52)

<400> SEQUENCE: 15
aatgggaggc ctagacgatt tttgcaacga tcctatcgcc gcaaagctcg tg 52

<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: primer
      LV226
<220> FEATURE:
<221> NAME/KEY: misc_feature
<222> LOCATION: (1)..(52)

<400> SEQUENCE: 16
aatgggaggc ctagacgatt tttgcaacga tcctatcgcc gcagaaaagc tc 52

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: primer
      LV227
<220> FEATURE:
<221> NAME/KEY: misc_feature
<222> LOCATION: (1)..(31)

<400> SEQUENCE: 17
aatgggaggc ctagacgatt ttaacgatcc t 31

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: primer
      118U250
<220> FEATURE:
<221> NAME/KEY: misc_feature
<222> LOCATION: (1)..(20)

<400> SEQUENCE: 18
cagccagggg aaaatgtggc 20

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: primer LV32
<220> FEATURE:
<221> NAME/KEY: misc_feature
<222> LOCATION: (1)..(27)

<400> SEQUENCE: 19
gattggatcc attctcttgg caatatg 27

<210> SEQ ID NO 20

-continued

```
<211> LENGTH: 21
<212> TYPE: DNA
<213> ORGANISM: Artificial Sequence
<220> FEATURE:
<223> OTHER INFORMATION: Description of Artificial Sequence: primer LV75
<220> FEATURE:
<221> NAME/KEY: misc_feature
<222> LOCATION: (1)..(21)

<400> SEQUENCE: 20

tctaggaatt ctagacgatc g                                            21


<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: primer
      LV182
<220> FEATURE:
<221> NAME/KEY: misc_feature
<222> LOCATION: (1)..(28)

<400> SEQUENCE: 21

ggattgaaaa tgcaattaat tcatgtat                                     28


<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: primer
      PRRSV57
<220> FEATURE:
<221> NAME/KEY: misc_feature
<222> LOCATION: (1)..(44)

<400> SEQUENCE: 22

tgctatcatg acagaagtca tctaaggacg accccattgc tcag                   44


<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: primer
      PRRSV58
<220> FEATURE:
<221> NAME/KEY: misc_feature
<222> LOCATION: (1)..(44)

<400> SEQUENCE: 23

gctaaaggct agcacgagct tttgtggagc cgtgctatca tgac                   44


<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: primer
      PRRSV59
<220> FEATURE:
<221> NAME/KEY: misc_feature
<222> LOCATION: (1)..(42)

<400> SEQUENCE: 24

atcccgtcac cacaaaatga atctatggct cccattgctc ag                     42


<210> SEQ ID NO 25
```

-continued

<211> LENGTH: 40
<212> TYPE: DNA
<213> ORGANISM: Artificial Sequence
<220> FEATURE:
<223> OTHER INFORMATION: Description of Artificial Sequence: primer
      PRRSV60
<220> FEATURE:
<221> NAME/KEY: misc_feature
<222> LOCATION: (1)..(40)

<400> SEQUENCE: 25
gctaaaggct agcacgagct cacctaaaat cccgtcacca 40

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: primer
      LV302
<220> FEATURE:
<221> NAME/KEY: misc_feature
<222> LOCATION: (1)..(25)

<400> SEQUENCE: 26
cttgacgata tcagagctga atggg 25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: primer
      LV303
<220> FEATURE:
<221> NAME/KEY: misc_feature
<222> LOCATION: (1)..(25)

<400> SEQUENCE: 27
cccattcagc tctgatatcg tcaag 25

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: primer
      LV306
<220> FEATURE:
<221> NAME/KEY: misc_feature
<222> LOCATION: (1)..(29)

<400> SEQUENCE: 28
gctaaggcta gcacgaggca aaaatcgtc 29

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: primer
      LV310
<220> FEATURE:
<221> NAME/KEY: misc_feature
<222> LOCATION: (1)..(19)

<400> SEQUENCE: 29
gtacgtactc tcaagcgtc 19

-continued

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: primer
LV311
<220> FEATURE:
<221> NAME/KEY: misc_feature
<222> LOCATION: (1)..(19)

<400> SEQUENCE: 30
gacgcttgag agtacgtac 19

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: primer
LV312
<220> FEATURE:
<221> NAME/KEY: misc_feature
<222> LOCATION: (1)..(20)

<400> SEQUENCE: 31
ctacggcgct tcagctttcg 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: primer
LV313
<220> FEATURE:
<221> NAME/KEY: misc_feature
<222> LOCATION: (1)..(20)

<400> SEQUENCE: 32
cgaaagctga agcgccgtag 20

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: primer
LV356
<220> FEATURE:
<221> NAME/KEY: misc_feature
<222> LOCATION: (1)..(31)

<400> SEQUENCE: 33
gcagtgggag gcctgatggg gtcgtcctta g 31

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: primer
LV357
<220> FEATURE:
<221> NAME/KEY: misc_feature
<222> LOCATION: (1)..(31)

<400> SEQUENCE: 34
ctaaggacga ccccatcagg cctcccactg c 31

-continued

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: primer LV358
<220> FEATURE:
<221> NAME/KEY: misc_feature
<222> LOCATION: (1)..(31)

<400> SEQUENCE: 35
cgtctaggcc tcccatcaag cttcccactg c 31

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: primer LV360
<220> FEATURE:
<221> NAME/KEY: misc_feature
<222> LOCATION: (1)..(33)

<400> SEQUENCE: 36
gcagtgggag gcctgatggg agccatagaa ttc 33

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: primer LV361
<220> FEATURE:
<221> NAME/KEY: misc_feature
<222> LOCATION: (1)..(32)

<400> SEQUENCE: 37
gaatctatgg ctcccatcag gcctcccact gc 32

<210> SEQ ID NO 38
<211> LENGTH: 162
<212> TYPE: PRT
<213> ORGANISM: Equine arteritis virus
<220> FEATURE:
<221> NAME/KEY: SIMILAR
<222> LOCATION: (1)..(162)
<223> OTHER INFORMATION: /note="M protein of EAV (EAV_ORF6_p)"

<400> SEQUENCE: 38

Met Gly Ala Ile Asp Ser Phe Cys Gly Asp Gly Ile Leu Gly Glu Tyr
1 5 10 15

Leu Asp Tyr Phe Ile Leu Ser Val Pro Leu Leu Leu Leu Leu Thr Arg
20 25 30

Tyr Val Ala Ser Gly Leu Val Tyr Val Leu Thr Ala Leu Phe Tyr Ser
35 40 45

Phe Val Leu Ala Ala Tyr Ile Trp Phe Val Ile Val Gly Arg Ala Phe
50 55 60

Ser Thr Ala Tyr Ala Phe Val Leu Leu Ala Ala Phe Leu Leu Leu Val
65 70 75 80

Met Arg Met Ile Val Gly Met Met Pro Arg Leu Arg Ser Ile Phe Asn
85 90 95

His Arg Gln Leu Val Val Ala Asp Phe Val Asp Thr Pro Ser Gly Pro

-continued

```
            100                 105                 110

Val Pro Ile Pro Arg Ser Thr Thr Gln Val Val Val Arg Gly Asn Gly
        115                 120                 125

Tyr Thr Ala Val Gly Asn Lys Leu Val Asp Gly Val Lys Thr Ile Thr
    130                 135                 140

Ser Ala Gly Arg Leu Phe Ser Lys Arg Thr Ala Ala Thr Ala Tyr Lys
145                 150                 155                 160

Leu Gln


<210> SEQ ID NO 39
<211> LENGTH: 171
<212> TYPE: PRT
<213> ORGANISM: Lactate dehydrogenase-elevating virus
<220> FEATURE:
<221> NAME/KEY: SIMILAR
<222> LOCATION: (1)..(171)
<223> OTHER INFORMATION: /note="M protein of LDV (LDV_ORF6_p)"

<400> SEQUENCE: 39

Met Gly Gly Leu Glu Phe Cys Asp Gln Thr Ser Trp Tyr Gln Ile Leu
  1               5                  10                  15

Ile Ala Phe Ser Leu Thr Tyr Thr Pro Ile Ala Ile Tyr Ser Leu Lys
             20                  25                  30

Val Phe Arg Gly Thr Leu Ala Gly Ile Val Asn Ile Phe Ile Phe Ile
         35                  40                  45

Asn Cys Cys Val Ser Phe Val Tyr Leu Met Tyr His His Ser Val Thr
     50                  55                  60

Asn Thr Val Ala Leu Ser Leu Gly Ala Val Ile Ala Leu Val Trp Gly
 65                  70                  75                  80

Ile Tyr Thr Leu Val Lys Ile Val Asn Trp Met Val Leu Arg Cys Arg
                 85                  90                  95

Leu Cys Phe Leu Gly Arg Ser Tyr Ile Leu Ala Pro Pro Ser His Val
            100                 105                 110

Asp Thr Ser Asp Gly Arg Gln Ser Leu Thr Thr Ser Ser Thr Thr Ala
        115                 120                 125

Phe Val Val Arg Lys Pro Gly Ser Thr Leu Val Asn Gly Gln Leu Val
    130                 135                 140

Pro Asp Phe Gln Arg Leu Val Leu Gly Gly Lys Lys Ala Val Ser Lys
145                 150                 155                 160

Gly Ala Val Asn Leu Leu Lys Tyr Val Ser Lys
                165                 170


<210> SEQ ID NO 40
<211> LENGTH: 173
<212> TYPE: PRT
<213> ORGANISM: Porcine reproductive and respiratory syndrome virus
<220> FEATURE:
<221> NAME/KEY: SIMILAR
<222> LOCATION: (1)..(173)
<223> OTHER INFORMATION: /note="M protein of PRRSV (PRRSV_Ter_)"

<400> SEQUENCE: 40

Met Gly Gly Leu Asp Asp Phe Cys Asn Asp Pro Ile Ala Ala Gln Lys
  1               5                  10                  15

Leu Val Leu Ala Phe Ser Ile Thr Tyr Thr Pro Ile Met Ile Tyr Ala
             20                  25                  30

Leu Lys Val Ser Arg Gly Arg Leu Leu Gly Leu Leu His Ile Leu Ile
         35                  40                  45
```

-continued

```
Phe Leu Asn Cys Ser Phe Thr Phe Gly Tyr Met Thr Tyr Val His Phe
     50                  55                  60

Gln Ser Thr Asn Arg Val Ala Leu Thr Leu Gly Ala Val Val Ala Leu
 65                  70                  75                  80

Leu Trp Gly Val Tyr Ser Phe Thr Glu Ser Trp Lys Phe Ile Thr Ser
                 85                  90                  95

Arg Cys Arg Leu Cys Cys Leu Gly Arg Arg Tyr Ile Leu Ala Pro Ala
            100                 105                 110

His His Val Glu Ser Ala Ala Gly Leu His Ser Ile Ser Ala Ser Gly
        115                 120                 125

Asn Arg Ala Tyr Ala Val Arg Lys Pro Gly Leu Thr Ser Val Asn Gly
    130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170


<210> SEQ ID NO 41
<211> LENGTH: 174
<212> TYPE: PRT
<213> ORGANISM: Porcine reproductive and respiratory syndrome virus
<220> FEATURE:
<221> NAME/KEY: SIMILAR
<222> LOCATION: (1)..(174)
<223> OTHER INFORMATION: /note="M protein of PRRSV (PRRSV_VR23)"

<400> SEQUENCE: 41

Met Gly Ser Ser Leu Asp Asp Phe Cys His Asp Ser Thr Ala Pro Gln
  1               5                  10                  15

Lys Val Leu Leu Ala Phe Ser Ile Thr Tyr Thr Pro Val Met Ile Tyr
             20                  25                  30

Ala Leu Lys Val Ser Arg Gly Arg Leu Leu Gly Leu Leu His Leu Leu
         35                  40                  45

Ile Phe Leu Asn Cys Ala Phe Thr Phe Gly Tyr Met Thr Phe Ala His
     50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Arg Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170


<210> SEQ ID NO 42
<211> LENGTH: 162
<212> TYPE: PRT
<213> ORGANISM: Simian hemorrhagic fever virus
<220> FEATURE:
<221> NAME/KEY: SIMILAR
<222> LOCATION: (1)..(162)
<223> OTHER INFORMATION: /note="M protein of SHFV (SHFV_ORF8_)"
```

-continued

<400> SEQUENCE: 42

```
Met Val Val Ser Leu Cys Ser Asp Pro Gly Tyr Thr Thr Leu Ala Phe
  1               5                  10                  15

Thr Ile Ala Pro Ala Leu Ile Ala Phe Leu Arg Tyr Phe Arg Pro Ser
             20                  25                  30

Val Arg Gly Phe Ile Cys Leu Val Cys Ile Ala Thr Leu Ala Tyr Ala
         35                  40                  45

Ala Thr Ala Phe Asn Glu His Ser Leu Ala Thr Leu Leu Thr Ile Gly
     50                  55                  60

Phe Ser Leu Val Tyr Leu Thr Tyr Lys Phe Ile Thr Trp Thr Ile Leu
 65                  70                  75                  80

Arg Val Arg Met Cys Trp Leu Gly Arg Gln Tyr Ile Thr Ala Pro Ser
                 85                  90                  95

Ser Met Val Glu Ser Ser Leu Gly Arg Leu Ala Ile Asn Ala Thr Gly
            100                 105                 110

Ser Thr Ala Val Val Thr Arg Arg Ser Gly Met Thr Ala Val Asn Gly
        115                 120                 125

Ser Leu Met Pro Asp Val Lys Arg Ile Ile Leu Asn Gly Arg Val Ala
    130                 135                 140

Ala Lys Arg Gly Leu Val Asn Leu Arg Lys Tyr Gly Trp Gln Thr Lys
145                 150                 155                 160

Asn Lys
```

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: GP5-M protein construct pABV437
<220> FEATURE:
<221> NAME/KEY: SITE
<222> LOCATION: (1)..(6)

<400> SEQUENCE: 43

```
Ala Glu Gln Trp Glu Ala
  1               5
```

<210> SEQ ID NO 44
<211> LENGTH: 56
<212> TYPE: DNA
<213> ORGANISM: Artificial Sequence
<220> FEATURE:
<223> OTHER INFORMATION: Description of Artificial Sequence: GP5-M protein construct pABV437
<220> FEATURE:
<221> NAME/KEY: misc_feature
<222> LOCATION: (1)..(56)

<400> SEQUENCE: 44

```
gctgagcaat gggaggccta gacgattttt gcaacgatcc tatcgccgca caaaag        56
```

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: GP5-M protein construct pABV437
<220> FEATURE:
<221> NAME/KEY: SITE
<222> LOCATION: (1)..(16)

-continued

<400> SEQUENCE: 45

Met Gly Gly Leu Asp Asp Phe Cys Asn Asp Pro Ile Ala Ala Gln Lys
1 5 10 15

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: GP5-M protein construct pABV857
<220> FEATURE:
<221> NAME/KEY: SITE
<222> LOCATION: (1)..(7)

<400> SEQUENCE: 46

Ala Glu Gln Trp Gly Arg Pro
1 5

<210> SEQ ID NO 47
<211> LENGTH: 59
<212> TYPE: DNA
<213> ORGANISM: Artificial Sequence
<220> FEATURE:
<223> OTHER INFORMATION: Description of Artificial Sequence: GP5-M protein construct pABV857
<220> FEATURE:
<221> NAME/KEY: misc_feature
<222> LOCATION: (1)..(59)

<400> SEQUENCE: 47
gctgagcaat ggggtcgtcc ttagatgact tctgtcatga tagcacggct ccacaaaag 59

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: GP5-M protein construct pABV857
<220> FEATURE:
<221> NAME/KEY: SITE
<222> LOCATION: (1)..(17)

<400> SEQUENCE: 48

Met Gly Ser Ser Leu Asp Asp Phe Cys His Asp Ser Thr Ala Pro Gln
1 5 10 15

Lys

<210> SEQ ID NO 49
<211> LENGTH: 50
<212> TYPE: DNA
<213> ORGANISM: Artificial Sequence
<220> FEATURE:
<223> OTHER INFORMATION: Description of Artificial Sequence: GP5-M protein constuct pABV707
<220> FEATURE:
<221> NAME/KEY: misc_feature
<222> LOCATION: (1)..(50)

<400> SEQUENCE: 49
gctgagcaat gggaggccta gaattttgtg atcaaacttc ctggtatcag 50

<210> SEQ ID NO 50
<211> LENGTH: 14
<212> TYPE: PRT
<213> ORGANISM: Artificial Sequence
<220> FEATURE:

-continued

<223> OTHER INFORMATION: Description of Artificial Sequence: GP5-M
      protein construct pABV707

<400> SEQUENCE: 50

Met Gly Gly Leu Glu Phe Cys Asp Gln Thr Ser Trp Tyr Gln
  1               5                   10

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: GP5-M
      protein construct pABV856
<220> FEATURE:
<221> NAME/KEY: SITE
<222> LOCATION: (1)..(6)

<400> SEQUENCE: 51

Ala Glu Gln Trp Glu Pro
  1               5

<210> SEQ ID NO 52
<211> LENGTH: 53
<212> TYPE: DNA
<213> ORGANISM: Artificial Sequence
<220> FEATURE:
<223> OTHER INFORMATION: Description of Artificial Sequence: GP5-M
      protein construct pABV856
<220> FEATURE:
<221> NAME/KEY: misc_feature
<222> LOCATION: (1)..(53)

<400> SEQUENCE: 52
gctgagcaat gggagccata gattcatttt gtggtgacgg gattttaggt gag            53

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: GP5-M
      protein construct pABV856
<220> FEATURE:
<221> NAME/KEY: SITE
<222> LOCATION: (1)..(15)

<400> SEQUENCE: 53

Met Gly Ala Ile Asp Ser Phe Cys Gly Asp Gly Ile Leu Gly Glu
  1               5                   10                  15

<210> SEQ ID NO 54
<211> LENGTH: 68
<212> TYPE: DNA
<213> ORGANISM: Artificial Sequence
<220> FEATURE:
<223> OTHER INFORMATION: Description of Artificial Sequence: GP5-M
      protein construct pABV871
<220> FEATURE:
<221> NAME/KEY: misc_feature
<222> LOCATION: (1)..(68)

<400> SEQUENCE: 54
gctgagcagt gggaagcttg atgggaggcc tagacgattt ttgcaacgat cctatcgccg     60
cacaaaag                                                              68

<210> SEQ ID NO 55
<211> LENGTH: 71

-continued

```
<212> TYPE: DNA
<213> ORGANISM: Artificial Sequence
<220> FEATURE:
<223> OTHER INFORMATION: Description of Artificial Sequence: GP5-M
      protein construct pABV872
<220> FEATURE:
<221> NAME/KEY: misc_feature
<222> LOCATION: (1)..(71)

<400> SEQUENCE: 55

gctgagcagt gggaagcttg atggggtcgt ccttagatga cttctgtcat gatagcacgg     60

ctccacaaaa g                                                          71


<210> SEQ ID NO 56
<211> LENGTH: 65
<212> TYPE: DNA
<213> ORGANISM: Artificial Sequence
<220> FEATURE:
<223> OTHER INFORMATION: Description of Artificial Sequence: GP5-M
      protein construct pABV873
<220> FEATURE:
<221> NAME/KEY: misc_feature
<222> LOCATION: (1)..(65)

<400> SEQUENCE: 56

gctgagcagt gggaagcttg atgggagcca tagattcatt ttgtggtgac gggattttag     60

gtgag                                                                 65
```